United States Patent [19]

Chen

[11] Patent Number: 5,242,424
[45] Date of Patent: Sep. 7, 1993

[54] DEVICE FOR USE IN CONTROLLING INTRAVENOUS DRIP

[76] Inventor: Yueh-Horng Chen, No. 39, Lane 84, Chung-Hsiao 2nd Rd., Ling-Ya Dist., Kaohsiung, Taiwan

[21] Appl. No.: 24,442

[22] Filed: Mar. 1, 1993

[51] Int. Cl.⁵ .............................................. A61M 5/14
[52] U.S. Cl. .................................... 604/251; 604/122; 604/127
[58] Field of Search ............... 604/122, 127, 251, 252, 604/253, 254, 255, 123

[56] References Cited

U.S. PATENT DOCUMENTS

| | | | |
|---|---|---|---|
| 3,216,418 | 11/1965 | Suslowiez | 604/127 |
| 3,776,229 | 12/1973 | McPhee | 604/127 |
| 3,965,895 | 6/1976 | Dabney | 604/127 |
| 4,175,558 | 11/1979 | Hess, III et al. | 604/127 |
| 4,332,247 | 6/1982 | Mittleman | 604/251 |
| 4,959,053 | 9/1990 | Jang | 604/127 |
| 5,031,654 | 7/1991 | Kobayashi | 604/127 |

Primary Examiner—Paul J. Hirsch
Attorney, Agent, or Firm—Jacobson, Price, Holman & Stern

[57] ABSTRACT

A device for use in controlling the intravenous drip comprises a cap and a dripping vessel. The cap is connected with a solution bottle of the intravenous drip by means of an upper connecting tube while the dripping vessel is in communication with a hypodermic needle by means of a lower connecting tube. The cap is provided thereon with a gas column having therein a gas duct in which a press rod is movably disposed. The gas in the upper connecting tube and the dripping vessel can be let out rapidly by means of the press rod.

1 Claim, 4 Drawing Sheets

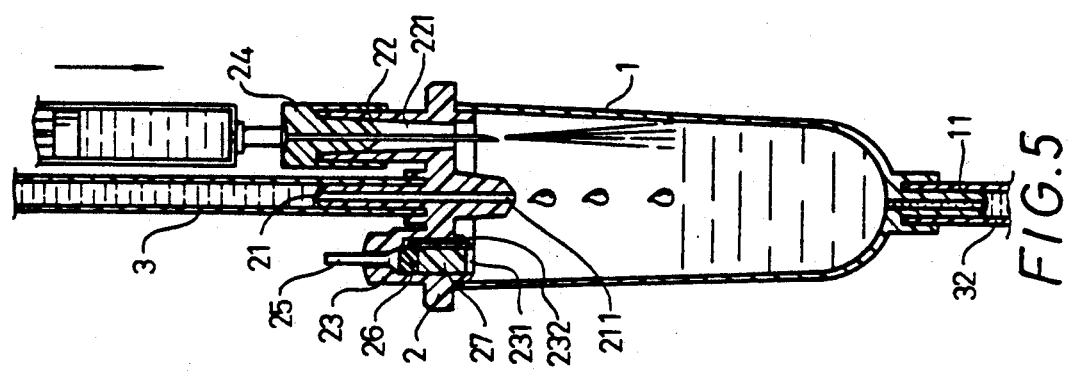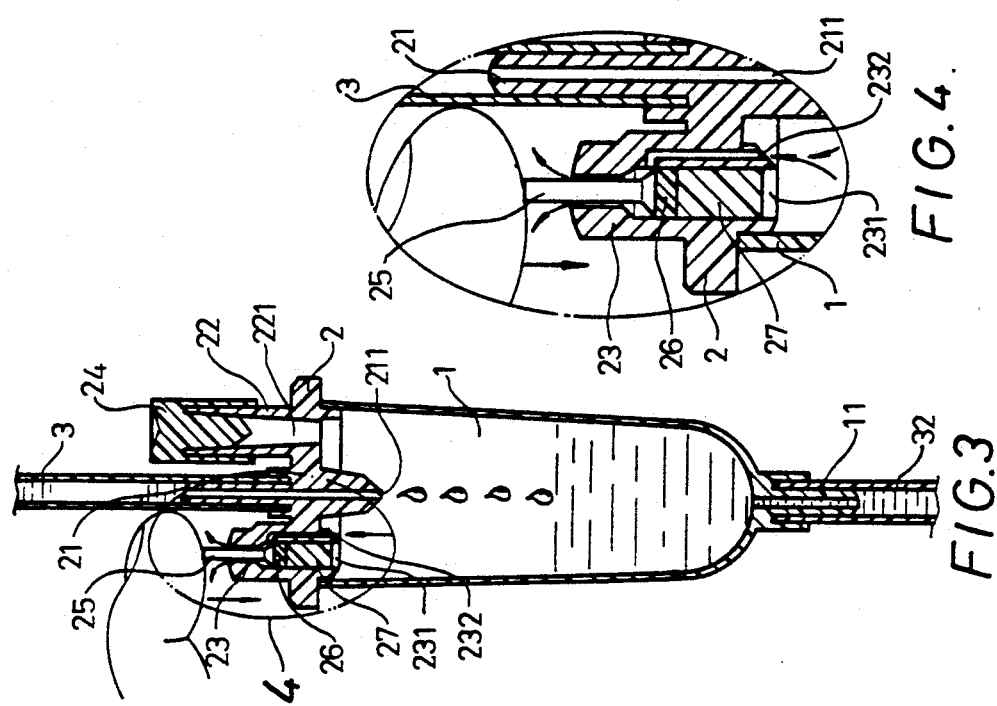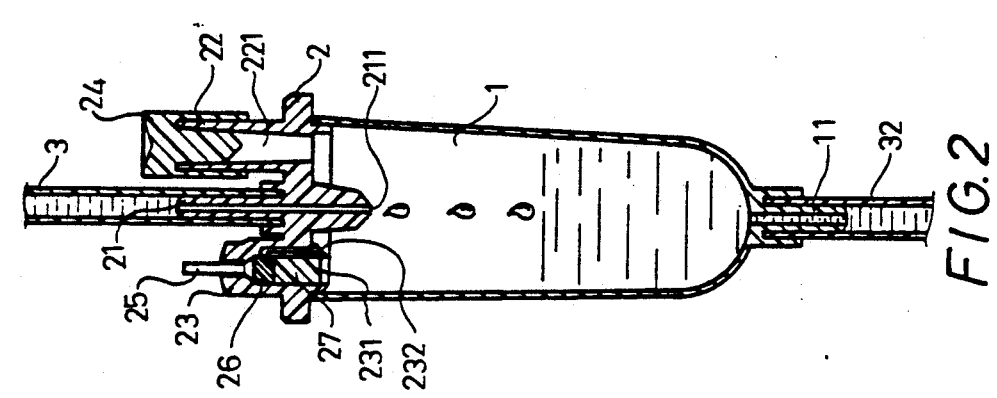

DEVICE FOR USE IN CONTROLLING INTRAVENOUS DRIP

FIELD OF THE INVENTION

The present invention relates to a medical treatment aid, and more particularly to a device for use in controlling the intravenous drip.

BACKGROUND OF THE INVENTION

As disclosed by Jang in the U.S. Pat. No. 4,959,053, an improved device for use in controlling the intravenous drip comprises a cap 2 having a horizontally oriented round tubular hole 23 in which a ring 25 is movably disposed. The movement of the ring 25 is movably disposed. The movement of the ring 25 in the round tubular hole 23 facilitates an entry of the air into the solution bottle via an air passage 28 so as to maintain a constant air pressure in the solution bottle. In order to safeguard a patient receiving the intravenous drip and to avert any possible mishap that might be brought about by a human negligence, the device described above is further provided with a dripping vessel 1 having therein a valve 4 capable of rising and descending along with the level of the solution contained in the dripping vessel 1. As a result, whenever the solution is about to be used up, the valve 4 descends to a level at which a conical surface 42 of the valve 4 is caused to obstruct the passage of the solution through a connecting tube 3, thereby bringing about an automatic interruption of the intravenous drip. Such a prior art device as described above is defective in design in that the dripping vessel 1 must be pressed and squeezed with the hands each time when the solution bottle of the intravenous drip is replaced, so as to force the air remaining in the dripping vessel 1 to flow into the new solution bottle. Without such a maneuver, the intravenous drip can not be resumed. It must be noted here that the job of pressing and squeezing the dripping vessel 1 must be done repeatedly by a skilled medical personnel. In addition, the prior art device for use in controlling the intravenous drip is generally devoid of the valve capable of automatically interrupting the intravenous drip. Therefore, a petient receiving the intravenous drip is often subjected to a mishap in which the air is permitted accidentally to enter the connecting tube or the body of the patient at such time when the solution in the solution bottle is exhausted. Moreover, whenever the solution bottle is replaced, the solution remaining in the connecting tube must be forced back into the solution bottle by shaking the device; otherwise the hypodermic needle must be removed from the patient and then injected hypodermically into the patient again.

SUMMARY OF THE INVENTION

It is therefore the primary objective of the present invention to provide a device for use in controlling the intravenous drip, which serves to overcome the shortcomings of the prior art device described above.

In keeping with the principles of the present invention, the foregoing objective of the present invention is attained by a device which comprises a dripping vessel, a cap that is united with the dripping vessel, an upper connecting tube, and a lower connecting tube. The solution of the intravenous drip is made available to the dripping vessel via the upper connecting tube while the solution in the dripping vessel is sent via the lower connecting tube to a hypodermic needle through which the solution is injected into a patient receiving the intravenous drip. The cap has a gas column provided with a lateral gas duct, which is unplugged by an elastic cushion when a press rod is caused to exert a pressure on the elastic cushion to contract. As a result, the gas in the dripping vessel and the upper connecting tube can be forced out to permit the dripping vessel to be replenished with the solution. On the other hand, the lateral gas duct of the cap is unplugged by the elastic cushion at such time when the elastic cushion is free from a pressure exerting thereon by the press rod, thereby bringing about a gradual resumption of the intravenous drip.

The foregoing objective and features of the present invention will be better understood by studying the following detailed description of the present invention in conjunction with the drawings provided herewith.

BRIEF DESCRIPTION OF THE DRAWINGS

FIG. 2 shows a sectional view of the present invention in combination.

FIG. 3 is a schematic view illustrating the working of the present invention as shown in FIG. 2.

FIG. 4 shows an enlarged view of a portion indicated by a circle 4 as shown in FIG. 3.

FIG. 5 is a sectional view of the present invention, showing that the replenishment of the solution of the intravenous drip is in progress.

DETAILED DESCRIPTION OF THE INVENTION

Figure 1:
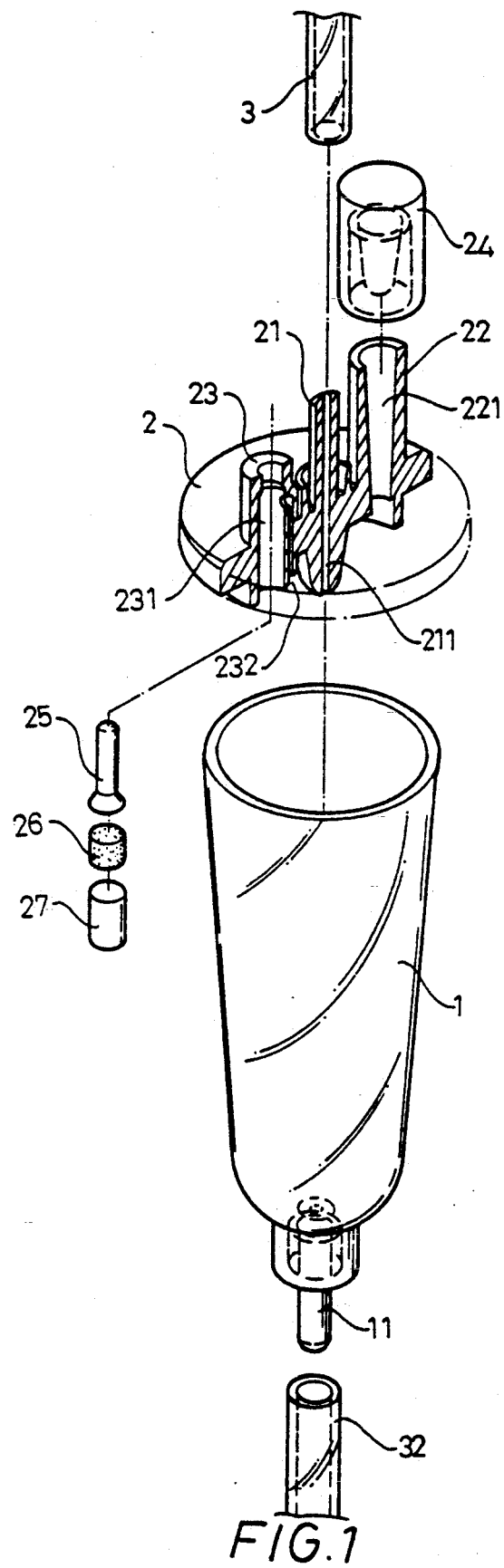
FIG. 1 shows an exploded view of the present invention.

Referring to FIG. 1, the present invention is shown to comprise a dripping vessel 1, a cap 2, an upper connecting tube 3, and a lower connecting tube 32.

The dripping vessel 1 of relatively large size has a bottom to which a solution releasing tube 11 is attached securely. The solution releasing tube 11 is so dimensioned as to fit securely into a lower connecting tube 32 through which the solution of the intravenous drip flows into a hypodermic needle 5. The dripping vessel 1 has a top portion so dimensioned as to fit securely into the cap 2.

The cap 2 is united with the top portion of the dripping vessel 1 in an airtight manner. The top of the cap 2 is provided uprightly with a supplying column 21, a solution filling column 22, and a gas column 23.

Figure 6:
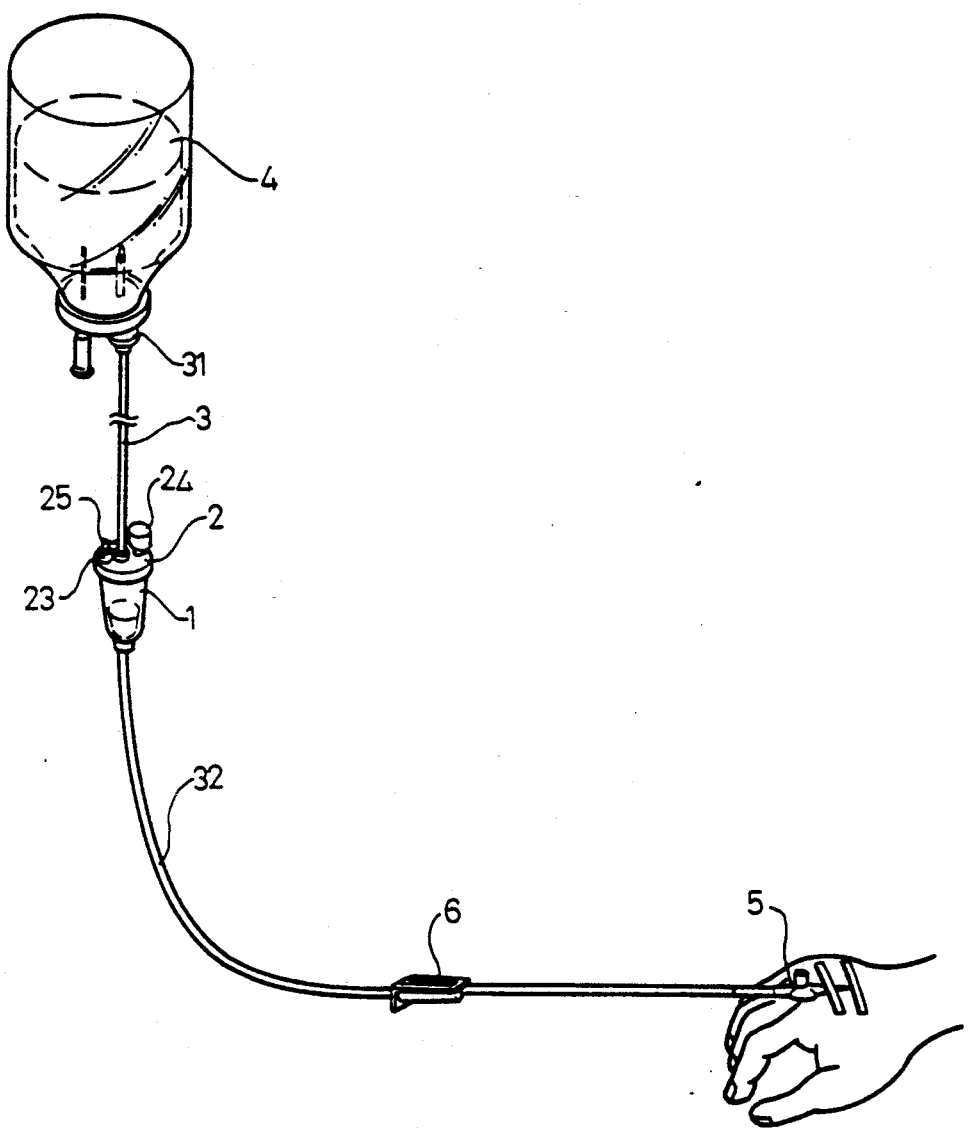
FIG. 6 shows an embodiment of the present invention.

The supplying oclum 21 has a top end fastened to the upper connecting tube 3 which is in turn connected with a needle head 31, as shown in FIG. 6. The top end of the needle head 31 is inserted into a solution bottle 4 so that the solution contained in the solution bottle 4 can be directed to flow into the dripping vessel 1 via a channel 211 of the supplying column 21. The solution filling column 22 is fitted over by a covering 24 made of a material soft enough to permit a needle to insert thereinto. The solution is injected into the dripping vessel 1 via a duct 221 of the solution filling column 22, as shown in FIG. 5. The gas column 23 is used for discharging the gas contained in the dripping vessel 1. The gas column 23 has a gas duct 231 running therethrough along the direction of the longitudinal axis of the gas column 23. Located by the gas duct 231 is a lateral gas duct 232 having one end in communication with the gas duct 231 and having another end in communication with the dripping vessel 1. The upper portion of the gas duct 231 has a smaller diameter so as to permit a press rod 25 to fit therinto in such a manner that the press rod 25 moves in the direction of the longitudinal axis of the gas duct 231, and that there is a clearance between the press rod 25 and the inner wall of the upper portion of the gas duct 231 in which the press rod 25 is received. The clearance between the press rod 25 and the inner wall of the upper portion of the gas duct 231 is such that the gas can flow therethrough. After the press rod 25 is disposed in the gas duct 231 in a manner described above, a cushion 26 of an elastic material such as rubber and a plug 27 are lodged in the gas duct 231, with one end of the cushion 26 being in contact with the press rod 25, and with the plug 27 being placed fixedly in the gas duct 231. As a result, when the press rod 25 is exerted when the press rod 25 is exerted on by an external force, the press rod 25 forces the elastic cushion 26 to contract. As soon as the press rod 25 is relieved of the external pressure, the elastic cushion 26 regains its original form so as to cause the press rod 25 to move back to its original position.

Under the circumstance that the lateral gas duct 232 of the gas column 23 of the cap 2 is obstructed by the elastic cushion 26, the solution contained in the solution bottle is permitted to drip at a regular speed into he dripping vessel 1 via the upper connecting tube 3 and the needle head 3 which remains in the solution bottle, as shown in FIG. 2.

Figure 7:
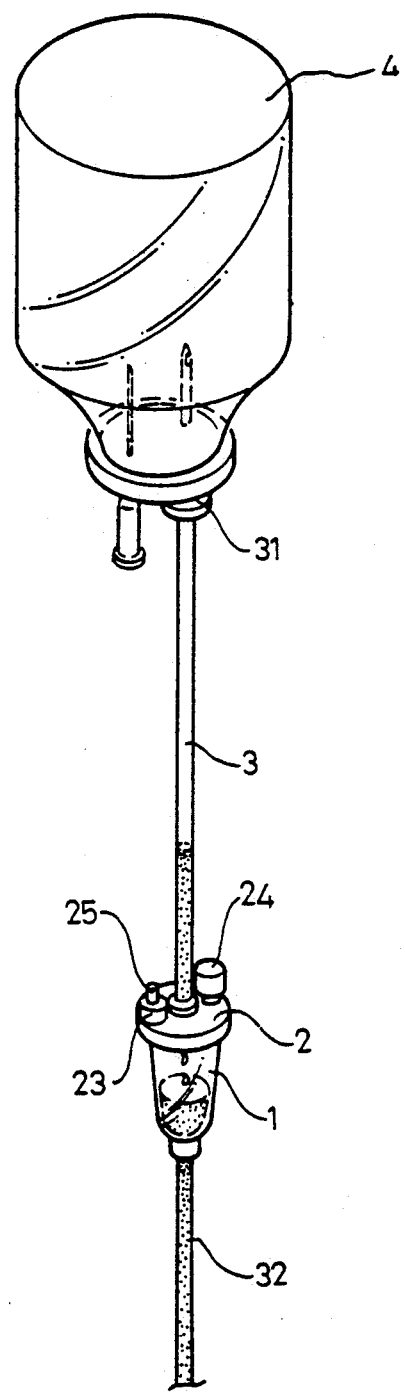
FIG. 7 is a schematic view showing that the solution in the solution bottle, as shown in FIG. 6, is used up.

The position of the dripping vessel 1 is slightly higher than that of the hypodermic needle 5 through which the solution is injected into a patient receiving the intravenous drip. As a result, the pressure of the solution in the dripping vessel 1 is almost equal to the blood pressure of the patient. Therefore, the solution stops flowing into the body of the patient at such time when the solution in the solution bottle 4 is exhausted, as illustrated in FIGS. 3 and 6. In the meantime, a small amount of the solution remains between the lower end of the upper connecting tube 3 and the dripping vessel 1 while the gas fills in between the upper end of the upper connecting tube 3 and the solution bottle 4, as shown in FIG. 7. Therefore, after the solution bottle 4 has been replaced, the gas in the upper connecting tube 3 must be expelled so as to allow the dripping vessel 1 to be replenished rapidly with the solution. As soon as the press rod 25 is pressed, as shown in FIGS. 3 and 4, the press rod 25 exerts a pressure on the elastic cushion 26, which is thus caused to contract. The contraction of the elastic cushion 26 results in the unplugging of the lateral gas uct 232, thereby permitting the gas in the dripping vessel 1 and the upper connecting tube 3 to flow out via the lateral gas duct 232, the gas duct 231 and the clearance between the press rod 25 and the inner wall of the gas duct 231. Upon the completion of the removal of the gas from the dripping vessel 1 and the upper connecting tube 3, the solution in the solution bottle 4 begins flowing rapidly into the dripping vessel 1. In the meantime, the press rod 25 is relieved of the pressure so that elastic cushion 26 is allowed to regain its original form so as to obstruct the lateral gas duct 232. As a result, the solution drips at a regular pace into the dripping vessel 1, as shown in FIG. 2.

The embodiment of the present invention is schematically shown in FIG. 6. The dripping vessel 1 and the cap 2 are so united that the cap 2 is connected with the solution bottle 4 by means of the upper connecting tube 3, and that the dripping vessel 1 is connected with the hypodermic needle 5 by means of the lower connecting tube 32 which is additionally provided with an adjusting apparatus 6 intended for use in controlling the flowing rate of the solution.

According to the present invention described above, it is apparent that an interruption of the intravenous drip is triggered automatically at such time when the solution in the solution bottle is used up, and that the gas in the upper connecting tube 3 or the dripping vessel 1 can be let out easily and rapidly after the solution bottle is replaced with a new one.

What is claimed is:

1. A device for use in controlling the intravenous drip comprising:

a dripping vessel of relatively large size having a bottom portion and a top portion, with said bottom portion being provided with a solution releasing tube having a top end fastened to said bottom portion and having a a bottom end coupled with a lower connecting tube, and with said top portion being so dimensioned as to fit into a cap in an airtight manner; and a cap dimensioned to fit over said top portion of said dripping vessel in an airtight manner and provided thereon with a solution supplying column, a solution filling column and a gas column, said solution supplying column having a top end coupled with a lower end of an upper connecting tube which has an upper end coupled with a needle head which is inserted into a solution bottle, said solution filling column having a duct passing through said cap and having a top fitted over with a covering of a soft material capable of being pierced through by an injection needle to facilitate an addition of a drug solution to said dripping vessel, said gas column having a gas duct passing through said cap and having a lateral gas duct communicating with said gas duct at one end thereof and with said dripping vessel at another end thereof, said gas duct having a top portion of a dimension for accommodating therein a press rod in such a manner that said press rod is capable of moving in the direction of the longitudinal axis of said gas duct and that there is a clearance between said press rod and an inner wall of said top portion of said gas duct which is further provided therein an elastic cushion and a plug, with said elastic cushion making contact at one end thereof with said press rod and at another end thereof with said plug which is lodged fixedly in said gas duct;

wherein said device is characterized in that said dripping vessel of said device is positioned at a level approximately corresponding to a level of a hypodermic needle through which said solution is injected into a patient receiving said intravenous drip, and that said press rod of said device can be pressed to exert a pressure on said elastic cushion to contract so as to prevent said elastic cushion from obstructing said lateral gas duct, thereby allowing a gas in said upper connecting tube and a gas in said dripping vessel to escape therefrom, and further that said press rod of said device can be relieved of a pressure to allow said elastic cushion to regain an original form thereof so as to obstruct said lateral gas duct.

* * * * *